United States Patent
Bowden et al.

(10) Patent No.: US 8,269,020 B2
(45) Date of Patent: Sep. 18, 2012

(54) PROCESSES FOR THE PREPARATION OF PYRAZOLES

(75) Inventors: Martin Charles Bowden, Bracknell (GB); Brian David Gott, Huddersfield (GB); Iacob Eremia Gutu, Chisinau (MD); David Anthony Jackson, Muenchwilen (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 173 days.

(21) Appl. No.: 12/666,179

(22) PCT Filed: Jun. 16, 2008

(86) PCT No.: PCT/EP2008/004829
§ 371 (c)(1), (2), (4) Date: Jun. 7, 2010

(87) PCT Pub. No.: WO2009/000441
PCT Pub. Date: Dec. 31, 2008

(65) Prior Publication Data
US 2010/0240907 A1    Sep. 23, 2010

(30) Foreign Application Priority Data
Jun. 27, 2007 (EP) .................................. 07012546

(51) Int. Cl.
*C07D 231/12* (2006.01)
*C07C 243/14* (2006.01)

(52) U.S. Cl. ..................................... 548/374.1; 564/250
(58) Field of Classification Search ........................ None
See application file for complete search history.

(56) References Cited

U.S. PATENT DOCUMENTS
7,994,341 B2 * 8/2011 Tobler et al. ............... 548/365.1

FOREIGN PATENT DOCUMENTS
WO    2005092885    10/2005

OTHER PUBLICATIONS

R. Brehme, et al.: "Reaktion von Acetophenonmonomethyl-und-dimethylhydrazonen mit dem Vilsmeier-Reagenz; Bildung von Pyrazol-4-carbiminiumsalzen: ein Beitrag zum Mechanismus" Journal Fur Praktische Chemie, vol. 342, No. 7, 2000, pp. 700-706.

* cited by examiner

*Primary Examiner* — Kamal Saeed
(74) *Attorney, Agent, or Firm* — Kody Jones

(57) ABSTRACT

The present invention relates to novel processes for the production of compounds of formula (I) wherein Hal and Hal' are independently selected from Cl and F, and $R^1$ is selected from Cl, F and H.

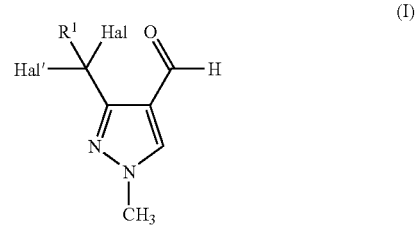

11 Claims, No Drawings

PROCESSES FOR THE PREPARATION OF PYRAZOLES

This is a 371 of International Application No. PCT/EP2008/004829 filed Jun. 16, 2008, which claims priority to EP07012546.3 filed Jun. 27, 2007, the contents of which are incorporated herein by reference.

The present invention relates to novel processes for the production of 3-di- and tri halomethyl-1-methyl-1H-pyrazole-4-carbaldehydes and 3-di- and tri halomethyl-1-methyl-1H-pyrazole-4-carboxylic acids, which are useful as intermediates in the preparation of fungicides, together with certain novel compounds useful as intermediates in such processes.

3-difluoromethyl-1-methyl-1H-pyrazole-4-carboxylic acid and 3-trifluoromethyl-1-methyl-1H-pyrazole-4-carboxylic acid are valuable intermediates in the preparation of pyrazolyl carboxanilide fungicides, as described, for example, in WO 03/070705 and WO 03/074491.

The aim of the present invention is therefore to provide novel processes for the production of key intermediates in the synthesis of 3-difluoromethyl-1-methyl-1H-pyrazole-4-carboxylic acid and 3-trifluoromethyl-1-methyl-1H-pyrazole-4-carboxylic acid that makes it possible to prepare said acids with high regioselectivity (in respect to the two nitrogen atoms of the pyrazole ring), in high yields and good quality in an economically advantageous and easily handled way.

SUMMARY OF THE INVENTION

According to a first aspect, the invention relates to a process for the preparation of a compound of formula (I)

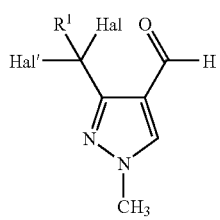

wherein Hal and Hal' are independently selected from Cl and F, and $R^1$ is selected from Cl, F and H, comprising reacting a compound of formula (II)

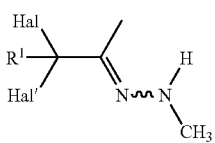

with a Vilsmeier reagent, wherein Hal, Hal' and $R^1$ are as defined above.

In a second embodiment, the invention relates to a compound of formula (I)

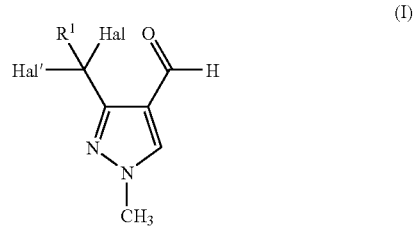

wherein Hal, Hal' and $R^1$ are as defined above.

In a third embodiment, the invention relates to a compound of formula (II)

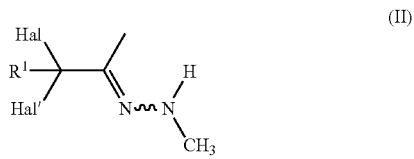

wherein Hal, Hal' and $R^1$ are as defined above.

DETAILED DESCRIPTION OF THE INVENTION

Vilsmeier Reagent

As used herein, the term "Vilsmeier reagent" refers to a compound of formula (III)

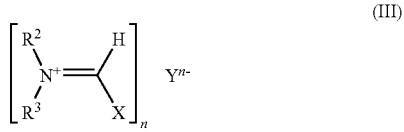

wherein $R^2$ and $R^3$ are independently selected from C1-6 alkyl and phenyl, X is halogen, $Y^{n-}$ is an anion, and n is 1, 2, 3 or 4.

Preferably, $R^2$ is methyl. Preferably, $R^3$ is methyl. More preferably, $R^2$ and $R^3$ are both methyl.

Preferably, X is chloro.

Preferably, $Y^{n-}$ is selected from $Cl^-$, $F^-$, $Br^-$, and $SO_4^{2-}$. More preferably, $Y^{n-}$ is $Cl^-$.

In a highly preferred embodiment, the Vilsmeier reagent is N-Chloromethylene-N,N-dimethyl ammonium chloride (IV)

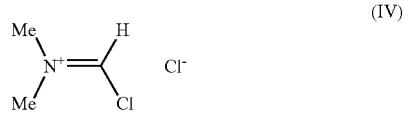

Certain Vilsmeier reagents may be purchased or prepared in advance, and the invention contemplates the use of these.

In a highly preferred embodiment, the Vilsmeier reagent is generated in situ. In situ generation of Vilsmeier reagents is suitably conducted by reaction of a formamide of formula (V)

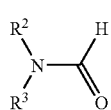

wherein $R^2$ and $R^3$ are as defined above, with an activating agent.

As used herein, the term "activating agent" refers to any compound capable of reacting with a compound of formula (V) to give a corresponding Vilsmeier reagent of formula (IV) above.

Preferred activating agents are phosphorous oxychloride, phosgene, thionyl chloride, phosphorous pentachloride and oxalyl chloride. Phosphorous oxychloride is the most preferred.

In a very preferred embodiment, the Vilsmeier reagent is generated in situ from the reaction of dimethyl formamide with phosphorous oxychloride.

Reaction Conditions

Preferably, the reaction of compound (II) with the Vilsmeier reagent occurs in a suitable solvent. Alternatively, the reaction may be conducted in the absence of a solvent.

Preferred solvents are dimethyl formamide, xylene, toluene, mesitylene, tert-butyl benzene, chlorobenzene, 1,2-dichlorobenzene and isohexane and combinations thereof. Very preferably, the solvent is dimethyl formamide.

Preferably, the Vilsmeier reagent is present in excess relative to the hydrazone (II). More preferably, the Vilsmeier reagent is present in an amount of at least 2 times the amount of hydrazone (II) on a molar basis. More preferably, the Vilsmeier reagent is present in an amount of between 2 and 10 times the amount of hydrazone (II) on a molar basis. More preferably, the Vilsmeier reagent is present in an amount of between 3 and 5 times the amount of hydrazone (II) on a molar basis. More preferably, the Vilsmeier reagent is present in an amount of about 4 times the amount of hydrazone (II) on a molar basis.

Preferably, the hydrazone (II) is added to the Vilsmeier reagent. The hydrazone (II) and the Vilsmeier reagent are preferably in solution. Preferably, cooling is employed during the addition step. Preferably, the reaction mixture is held at 5-10° C. during the addition step. Preferably, the addition takes place over from 1 to 6 hours, more preferably over about 4 hours.

Subsequent to the addition of the hydrazone (II) to the Vilsmeier reagent, the reaction is allowed to continue. The skilled person will be aware that it may be advantageous to monitor the course of the reaction. Suitable techniques are set out in *Experimental Organic Chemistry standard and microscale* (2nd Edition), L. M. Harwood, C. J. Moody, and J. M. Percy, Blackwell Scientific, 1999, and include for example thin layer chromatography, gas chromatography, and high performance liquid chromatography (HPLC).

Preferably, reaction is continued for between 1 and 48 hours, more preferably from 6 to 24 hours, more preferably for about 12 hours.

Preferably, the reaction is conducted under an inert atmosphere. More preferably, the reaction is conducted under a nitrogen atmosphere.

Preferably, the reaction is heated. More preferably, the reaction is held at between 25 and 150° C. More preferably, the reaction is held at between 50 and 125° C. More preferably, the reaction is held at between 75 and 85° C.

The skilled person will be aware that work up of the reaction mixture may be necessary or desirable to isolate the aldehyde (I), if isolation is intended. Suitable work up procedures are described for example in *Experimental Organic Chemistry standard and microscale* (2nd Edition), L. M. Harwood, C. J. Moody, and J. M. Percy, Blackwell Scientific, 1999.

The skilled person will also be aware of purification techniques suitable for purifying the aldehyde (I). Suitable techniques include recrystallisation, distillation, and chromatography.

Oxidation to Carboxylic Acid

In a preferred embodiment, the process of the invention comprises a further step of oxidizing the aldehyde of formula (I) to the corresponding carboxylic acid (VI)

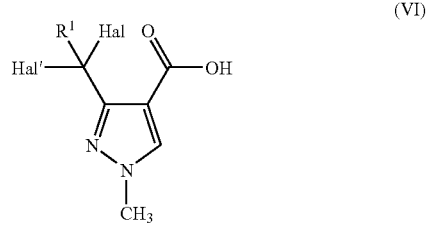

or a salt form thereof.

Many suitable reaction conditions exist for the oxidation of aldehydes to carboxylic acids. Suitable methods are disclosed for example in *Advanced Organic Chemistry*, J. March, John Wiley and Sons, 1992, pages 701-703.

Suitable oxidants include sodium permanganate, potassium permanganate, chromic acid, bromine, peroxides, hypochlorites and oxygen. Preferably, the oxidant is a peroxide. More preferably, the oxidant is hydrogen peroxide.

Preferably, the oxidant is employed in excess relative to the aldehyde (I). More preferably, the oxidant is employed in an amount of at least 2 times the amount of aldehyde (I) on a molar basis. More preferably, the oxidant is employed in an amount of between 5 and 50 times the amount of aldehyde (I) on a molar basis. More preferably, the oxidant is employed in an amount of between 10 and 20 times the amount of aldehyde (I) on a molar basis.

Preferably the reaction takes place in the presence of base. Preferred bases include alkali and alkaline earth metal hydroxides and carbonates. More preferred bases are sodium hydroxide and potassium hydroxide. A very preferred base is sodium hydroxide.

A very preferred combination of oxidant and base is hydrogen peroxide and sodium hydroxide.

Preferably, the oxidation reaction is carried out in a suitable solvent. Water is a preferred solvent.

Again, the skilled person will be aware of techniques for monitoring the course of the oxidation reaction in order to judge when it is complete.

In one embodiment of the invention, the aldehyde (I) is oxidized directly to the carboxylic acid (VI) without isolation of aldehyde (I) in a "one pot" procedure.

In certain embodiments, oxidation of the aldehyde (I) may result in a salt form of carboxylic acid (VI), rather than the free acid. In these embodiments, a step of treatment with acid may be used to convert the salt form to the free acid. Hydrochloric acid is preferred.

The skilled person will be aware that work up of the reaction mixture may be necessary or desirable to isolate the carboxylic acid (VI). Suitable work up procedures are described for example in *Experimental Organic Chemistry* standard and microscale (2nd Edition), L. M. Harwood, C. J. Moody, and J. M. Percy, Blackwell Scientific, 1999.

The skilled person will also be aware of purification techniques suitable for purifying the carboxylic acid (VI). Suitable techniques include recrystallisation, distillation, and chromatography.

Preparation of Hydrazone (II)

Hydrazone (II) is suitably prepared by condensation of ketone (VII)

(VII)

with methyl hydrazine.

The reaction is preferably carried out in a solvent. Preferred solvents are dimethyl formamide, xylene, toluene, mesitylene, tert-butyl benzene, chlorobenzene, 1,2-dichlorobenzene and isohexane. Most preferably, the solvent is dimethyl formamide.

Preferably, methyl hydrazine is used in an amount of 0.5 to 10 equivalents relative to the amount of ketone (VII) on a molar basis. More preferably, methyl hydrazine is used in an amount of 0.7 to 5 equivalents relative to the amount of ketone (VII) on a molar basis. More preferably, methyl hydrazine is used in an amount of 0.8 to 2 equivalents relative to the amount of ketone (VII) on a molar basis. More preferably, methyl hydrazine is used in an amount of 0.9 to 1.1 equivalents relative to the amount of ketone (VII) on a molar basis.

The reaction is preferably carried out in the presence of an acid. Preferred acids are organic acids. More preferred are formic acid, acetic acid or propionic acid. Alternatively, inorganic acids, including hydrochloric acid or sulphuric acid may be used.

Preferred amounts of acids are 0.05 to 1 equivalents relative to the amount of ketone (VII), more preferably from 0.1 to 0.5 equivalents, most preferably about 0.2 equivalents.

Preferably, the reaction is held at between 0 and 150° C. More preferably, the reaction is held at between 10 and 30° C. More preferably, the reaction is held at between 20 and 25° C.

Again, the skilled person will be aware of techniques for monitoring the course of the oxidation reaction in order to judge when it is complete. HPLC is particularly useful in this context.

The reaction time according to the invention is preferably from 1 to 48 hours, more preferably from 1 to 18 hours.

The skilled person will be aware that work up of the reaction mixture may be necessary or desirable to isolate the hydrazone (II), if isolation is intended. Suitable work up procedures are described for example in *Experimental Organic Chemistry standard and microscale* (2nd Edition), L. M. Harwood, C. J. Moody, and J. M. Percy, Blackwell Scientific, 1999.

The skilled person will also be aware of purification techniques suitable for purifying the hydrazone (II). Suitable techniques include recrystallisation, distillation, and chromatography.

In a very preferred embodiment, the hydrazone (II) is utilized directly in the subsequent reaction with Vilsmeier reagent without isolation. The hydrazone (II) may, however, be isolated according to techniques known in the art if desired.

Halogen Exchange.

In one embodiment of the invention, the reaction sequence includes a halogen exchange step.

The term "halogen exchange", as used herein, refers to a reaction wherein halogen atoms of one element are exchanged for halogen atoms of a second, different element.

Preferably, chlorine atoms are exchanged for fluorine atoms.

Halogen exchange may be conducted at any suitable step of the reaction sequence.

In a preferred embodiment, halogen exchange is effected on 3-dichloromethyl-1-methyl-1H-pyrazole-4-carbaldehyde (VIII) to give 3-difluoromethyl-1-methyl-1H-pyrazole-4-carbaldehyde (IX).

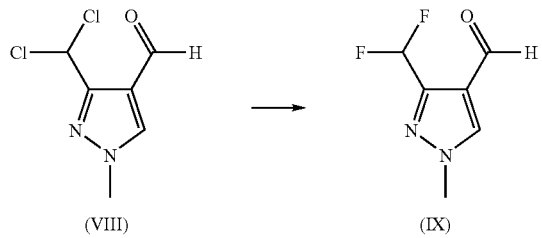

In an alternative embodiment, halogen exchange is effected on 3-dichloromethyl-1-methyl-1H-pyrazole-4-carboxylic acid (X) or a salt form thereof to give 3-difluoromethyl-1-methyl-1H-pyrazole-4-carboxylic acid (XI).

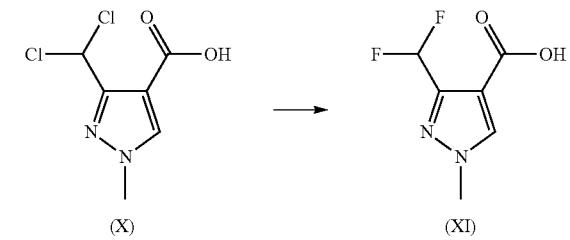

Halogen exchange may be conducted under a variety of conditions. Preferably, halogen exchange is conducted in the presence of a source of F" ions. Preferred reagents are AgF, KF, HgF$_2$, Bu$_4$N$^+$HF$^{2-}$, BrF$_3$, Et$_3$N.2HF, Et$_3$N.3HF and HF plus SbF$_3$. A very highly preferred reagent is Et$_3$N.3HF.

The halogen exchange reaction is optionally conducted in a solvent. Alternatively, and preferably, the reaction is conducted under solvent-free conditions.

Preferably, the reaction is held at between 0 and 250° C. More preferably, the reaction is held at between 50 and 200° C. More preferably, the reaction is held at between 125 and 175° C. Most preferably, the reaction is held at about 150° C.

Again, the skilled person will be aware of techniques for monitoring the course of the halogen exchange reaction in order to judge when it is complete. HPLC is particularly useful in this context.

The skilled person will be aware that work up of the reaction mixture may be necessary or desirable to isolate the product of the halogen exchange reaction, if isolation is intended. Suitable work up procedures are described for example in *Experimental Organic Chemistry standard and microscale* (2nd Edition), L. M. Harwood, C. J. Moody, and J. M. Percy, Blackwell Scientific, 1999. The skilled person will also be aware of purification techniques suitable for purifying the reaction product. Suitable techniques include recrystallisation, distillation, and chromatography.

Preferred Embodiments

In a preferred embodiment of the invention, $R^1$ is hydrogen.

In a preferred embodiment of the invention, Hal and Hal' are fluorine. Preferably, Hal and Hal' are fluorine and $R^1$ is hydrogen.

In this embodiment, the reaction sequence is shown in scheme 1. 1,1-difluoroacetone (XII) reacts with methyl hydrazine to give the corresponding hydrazone (XIII). Reaction of (XIII) with Vilsmeier reagent gives 3-difluoromethyl-1-methyl-1H-pyrazole-4-carbaldehyde (IX). Oxidation of (IX) gives 3-difluoromethyl-1-methyl-1H-pyrazole-4-carboxylic acid (XI) or a salt form thereof.

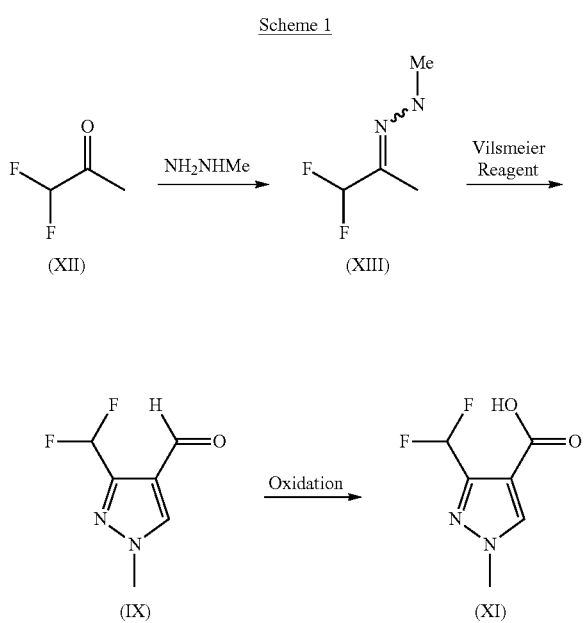

Scheme 1

In an alternative preferred embodiment of the invention, Hal, Hal' and $R^1$ are fluorine.

In this embodiment, the reaction sequence is shown in scheme 2. 1,1,1-trifluoroacetone (XIV) reacts with methyl hydrazine to give the corresponding hydrazone (XV). Reaction of (XV) with Vilsmeier reagent gives 3-trifluoromethyl-1-methyl-1H-pyrazole-4-carbaldehyde (XVII). Oxidation of (XVII) gives 3-trifluoromethyl-1-methyl-1H-pyrazole-4-carboxylic acid (XVIII) or a salt form thereof.

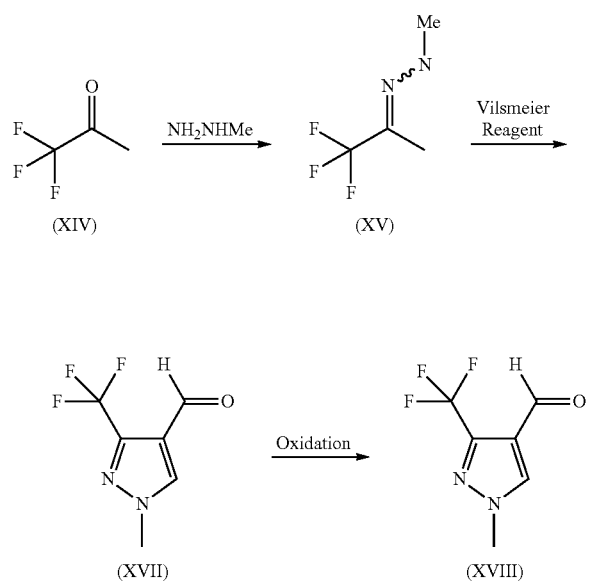

Scheme 2

In an alternative preferred embodiment, Hal and Hal' are both Cl, and $R^1$ is hydrogen.

In this embodiment, the reaction sequence is shown in scheme 3. In this embodiment, oxidation and halogen exchange steps may occur in either order to arrive at the same product.

In scheme 3, 1,1-dichloroacetone (XIX) reacts with methyl hydrazine to give the corresponding hydrazone (XX). Reaction of (XX) with Vilsmeier reagent gives 3-dichloromethyl-1-methyl-1H-pyrazole-4-carbaldehyde (VIII).

Oxidation of (VIII) gives 3-dichloromethyl-1-methyl-1H-pyrazole-4-carboxylic acid (X) or a salt form thereof. Halogen exchange furnishes 3-difluoromethyl-1-methyl-1H-pyrazole-4-carboxylic acid (XI).

Alternatively, halogen exchange of (VIII) 3-difluoromethyl-1-methyl-1H-pyrazole-4-carbaldehyde (IX). Oxidation furnishes 3-difluoromethyl-1-methyl-1H-pyrazole-4-carboxylic acid (XI).

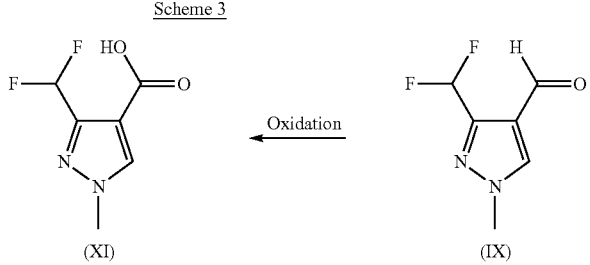

Scheme 3

-continued

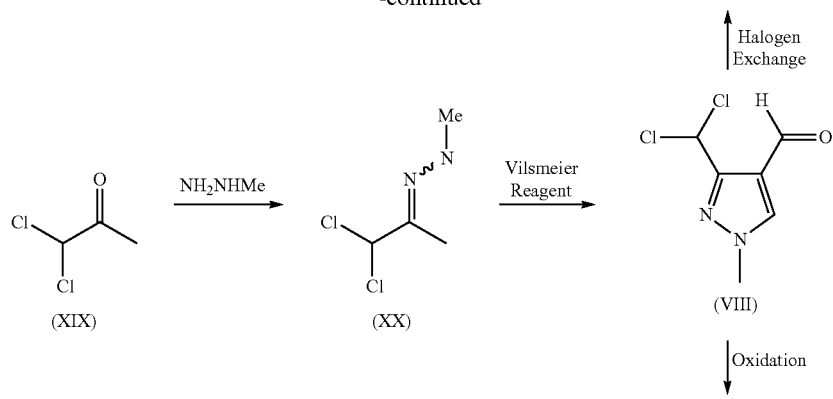

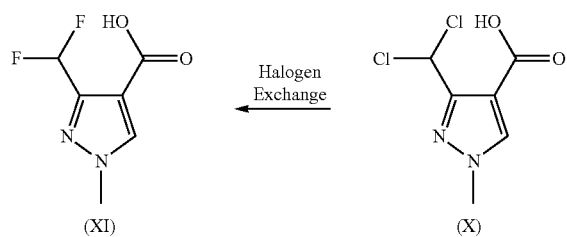

In a preferred embodiment, the present invention accordingly relates to a process for the production of a compound of formula XI

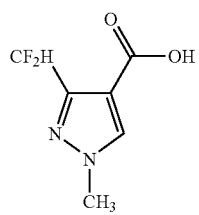
(XI)

which comprises a1) reacting a compound of formula XII (1,1-difluoroacetone)

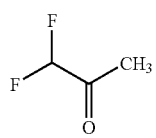
(XII)

with methylhydrazine to form a compound of formula XIII (N-[2,2-difluoro-1-methyl-ethylidene]-N'-methyl-hydrazine)

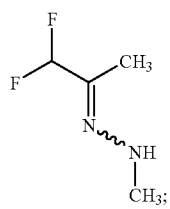
(XIII)

a2) reacting the compound of formula (XIII) with dimethyl formamide and an activating agent to give a compound of formula (IX) (3-difluoromethyl-1-methyl-1H-pyrazole-4-carbaldehyde)

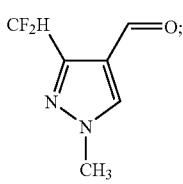
(IX)

and a3) oxidizing the compound of formula (IX) with an oxidizing agent in the presence of a base to the compound of formula (XI).

Process Step a1):

Process step a1 as defined above is preferably carried out at a temperature range of from 0° C. to 50° C., more preferably from 10° C. to 25° C.

The reaction is conveniently carried out in an inert solvent. Preferred inert solvents are, dimethyl formamide, xylene, toluene, mesitylene, tert-butyl benzene, chlorobenzene, 1,2-dichlorobenzene and isohexane; more preferably dimethyl formamide.

In the reaction according to the invention, methylhydrazine can be used in equimolar amounts, in sub-equimolar amounts or in excess relative to compounds of formula IV, preferably methylhydrazine is used in equimolar amounts.

The reaction is preferably carried out in the presence of an acid. Suitable acids are organic acids, such as, for example, formic acid, acetic acid or propionic acid; or inorganic acids, such as, for example, hydrochloric acid or sulfuric acid. Preferably, the acid is an organic acids more preferably, the acid is acetic acid. A preferred amount of acid is from 0.05 to 1 equivalents relative to compounds of formula XII, more preferably from 0.1 to 0.5 equivalents.

The reaction time according to the invention is preferably from 1 to 48 hours, more preferably from 1 to 18 hours, still more preferably 1 to 5 hours.

The reaction according to the invention can be carried out at atmospheric, elevated or reduced pressure. In one embodiment of the invention the reaction is carried out at atmospheric pressure.

Preferably, the compound of formula XIII is not isolated, but consumed in situ in process step a2).

Process Step a2):

Suitable activating agents are, for example, phosphorous oxychloride, phosgene or thionyl chloride; preferably phosphorous oxychloride.

The reaction according to the invention is preferably carried out in a temperature range of from 0° C. to 130° C., especially from 75° C. to 100° C.

The reaction is conveniently carried out in an inert solvent. Preferred inert solvents are the solvents used for process step a1).

In the reaction according to the invention, the activating agent, preferably phosphorous oxylchloride, is typically used in excess relative to compounds of formula XIII, preferably in a 2-fold to 6-fold excess.

The reaction time for the reaction according to the invention is generally from 1 to 48 hours, preferably from 1 to 24 hours, more preferably 1 to 18 hours.

The reaction according to the invention can be carried out at normal, elevated or reduced pressure. In one embodiment of the invention the reaction is carried out at normal pressure.

Process Step a3):

A suitable oxidizing agent for process step a3) is, for example, hydrogen peroxide. Suitable amounts of the oxidizing agent are, for example, at least 1 equivalent; preferably, from 10 to 20 equivalents.

Suitable bases are, for example, hydroxide bases are, for example alkali or earth alkali hydroxides, such as NaOH or KOH, with preference being given to NaOH. Suitable amounts of base are, for example, from 1 to 10 equivalents relative to compounds of formula IX, especially from 2 to 5 equivalents, and very especially about 4 equivalents.

The reaction is conveniently carried out in an inert solvent. Suitable inert solvents are, for example, water; alcohols, such as methanol, ethanol, propanol or isopropanol; or aprotic solvents, such as tetrahydrofuran, tert-butyl methyl ether, dioxane or toluene; and mixtures thereof; water is especially preferred.

Temperatures are generally from 0° C. to 120° C., with preference being given to a range from 0° C. to 100° C. and special preference to a range from 20° C. to 60° C. In one embodiment, the temperatures are in a range from 40 to 50° C.

The reaction may be carried out at atmospheric pressure or at elevated pressure.

The reaction time for that reaction is generally from 1 to 60 hours, preferably from 1 to 6 hours.

The first embodiment of the present invention makes it possible to produce compounds of formula I in a high yield, with a high degree of regioselectivity and at low cost.

The compounds of formula II are valuable intermediates for the preparation of compounds of formula I and were developed specifically for the present process according to the invention. The present invention accordingly relates also to those compounds.

A further aspect of the first embodiment is a process for the production of a compound of formula I, which comprises a1) reacting a compound of formula VII with methylhydrazine in the presence of an inert solvent to form a compound of formula II; and a2) converting that compound with phosphorous oxychloride and dimethyl formamide into the compound of formula I.

In said aspect process steps a1) and a2) are performed as described above.

The following non-limiting examples illustrate the invention in more detail. All following %-values are (w/w)-values unless noted otherwise.

EXAMPLE 1

Preparation of 3-Difluoromethyl-1-methyl-1H-pyrazole-4-carbaldehyde (IX)

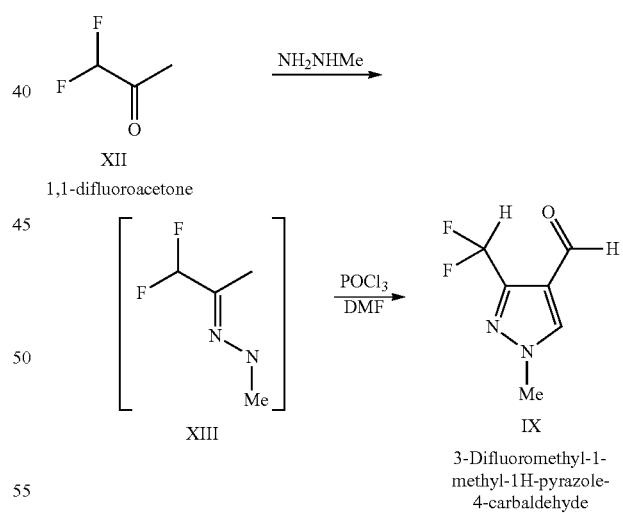

3-Difluoromethyl-1-methyl-1H-pyrazole-4-carbaldehyde

A 3-neck 500 ml round bottomed flask was fitted with a magnetic stirrer, thermometer and nitrogen atmosphere. 1,1-Difluoroacetone (compound of formula XII) (10.0 g), dimethylformamide (227 g) and acetic acid (1.35 g) were charged to the reactor. Methyl hydrazine (4.83 g) was added to the agitated solution and the reaction stirred at ambient temperature overnight. This gave the desired hydrazone intermediate (compound of formula XIII) with >99% consumption of starting material. The reaction mass was divided into two equal parts, and one half was processed as described below: a second 3-neck 500 ml round bottomed flask was fitted with a magnetic stirrer, condenser, thermometer and nitrogen atmosphere. Dimethylformamide (114 g) was charged to the reactor and heated to 50° C. Phosphorous oxychloride (66.1 g) was added over 0.75 hr with stirring at 45-50° C. The reaction was held at 50° C. for 1 hr then cooled to 10° C. The hydrazone (compound of formula XIII) solution prepared above was charged over 4 hr, maintaining the temperature at 5-10° C. The reaction was stirred at 80° C. overnight and then cooled to ambient temperature. Dichloromethane (500 ml) and ice (330 g) were charged to a jacketed 3 liter reactor fitted with a mechanical agitator. The reaction mass was charged over 0.5 hr to the ice/dichloromethane mixture with stirring. The pH was adjusted to 9.8 by addition of 20% sodium hydroxide solution (220 ml), resulting in some precipitation of solid. Further dichloromethane (300 ml) and water (750 ml) were charged and the mixture filtered. The dichloromethane layer was washed with water, and the aqueous layer extracted with dichloromethane. The combined dichloromethane layers were washed with water, dried ($MgSO_4$) and concentrated in vacuo [65% yield of desired product (compound of formula IX)–quantitative HPLC]. DMF removal (70° C., 3-5 mbar) in a Kugelrohr distillation apparatus gave the desired product (compound of formula IX) as a dark brown oil [53% yield of desired–quantitative HPLC].

MS: 42, 51, 69, 77, 83, 112, 131, 141, 159, 160 ($M^+$)

$^1$H NMR ($CDCl_3$): 4.00 (s, 3H, $NCH_3$), 6.88 (t, 1H, $CHF_2$), 7.75 (S, 1H, Ar$\underline{H}$), 10.0 (s, 1H, $C\underline{H}O$)

EXAMPLE 2

Preparation of 3-Difluoromethyl-1-methyl-1H-pyrazole-4-carboxylic acid (XI)

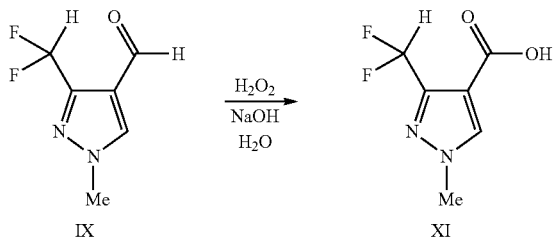

A 3-neck 250 ml round bottomed flask was fitted with a magnetic stirrer and thermometer. Water (130 g), the product of example 1 (compound of formula IX) (6.50 g) and aqueous sodium hydroxide (8.17 g) were charged to the reactor, and the resulting solution heated to 40-45° C. A 35% hydrogen peroxide solution (39 g) was added over 1 hr, and the mixture then stirred at 40-45° C. for 0.5 hr [83% yield of desired product (compound of formula XI)–quantitative HPLC]. The pH of the reaction mass was adjusted to 2.5 by addition of 36% aqueous hydrochloric acid solution. The resulting precipitate was isolated by filtration and washed with water. Drying (60° C., 10 mbar) gave the desired product (XI) as pale yellow, free-flowing powder [69% yield of desired product–quantitative HPLC].

MS: 42, 51, 69, 80, 88, 100, 108, 128, 137, 159, 176 ($M^+$)

$^1$H NMR ($d_6$-acetone): 3.98 (s, 3H, $NCH_3$), 7.21 (t, 1H, $C\underline{H}F_2$), 8.25 (S, 1H, Ar$\underline{H}$), 11.2 (broad s, 1H, $CO_2\underline{H}$)

EXAMPLE 3

Preparation of 3-Dichloromethyl-1-methyl-1H-pyrazole-4-carbaldehyde (VIII)

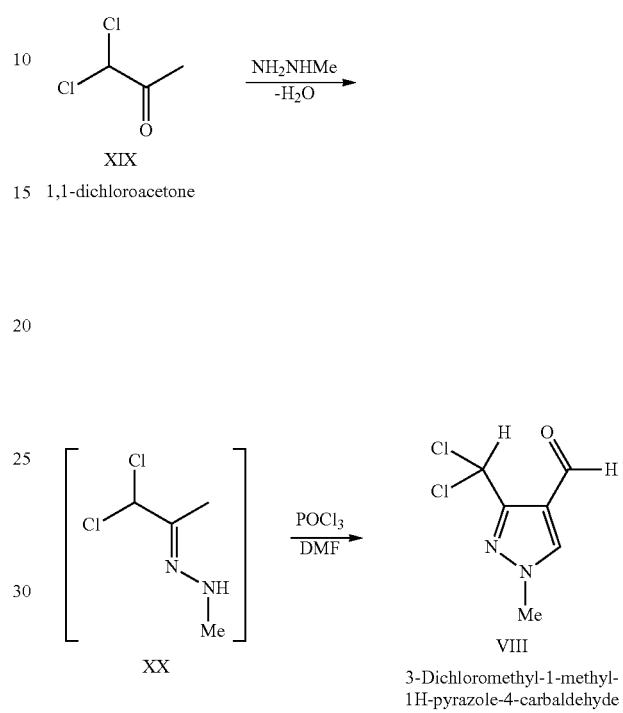

A 50 ml round bottomed flask was fitted with a magnetic stirrer, thermometer and nitrogen atmosphere. Dimethylformamide (30 ml) and 1,1-dichloroacetone (XIX) (3.05 g) were charged to the reactor. Methylhydrazine (1.25 g) was added slowly to the agitated solution, maintaining the mixture below 25° C. The reaction was stirred at ambient temperature for 0.75 h to give the desired hydrazone intermediate (XX). A 150 ml round bottomed flask was fitted with a magnetic stirrer, condenser, thermometer and nitrogen atmosphere. Dimethylformamide (60 ml) was charged to the reactor and heated to 50° C. Phosphorous oxychloride (15.0 g) was added via syringe pump. The reaction was stirred at 50° C. for 1 h then cooled to 10° C. The hydrazone (compound of formula XX) solution prepared as described above was charged immediately, maintaining the temperature at 5-10° C. The reaction was stirred at 80° C. for 5 h and then cooled to ambient temperature. The reaction mass was divided into two equal parts. Dichloromethane (100 ml), water (100 ml) and 10% aqueous sodium bicarbonate solution (150 ml) were charged to a glass vessel. The first half of the reaction mass was added and the pH adjusted to 7-8 with further sodium bicarbonate solution. This procedure was repeated with the second half of the reaction mass. The combined organic layers were washed with water (2×100 ml), dried ($MgSO_4$) and concentrated in vacuo. The compound of formula VIII was analyzed by MS and NMR.

MS: 42, 50, 85, 94, 122, 157, 192 ($M^+$)

$^1$H NMR (D7-DMF): 3.97 (s, 3H, $NCH_3$), 7.20 (s, 1H, $C\underline{H}Cl_2$), 8.05 (S, 1H, Ar$\underline{H}$), 10.03 (s, 1H, $C\underline{H}O$)

EXAMPLE 4

Preparation of 3-Difluoromethyl-1-methyl-1H-pyrazole-4-carbaldehyde (IX)

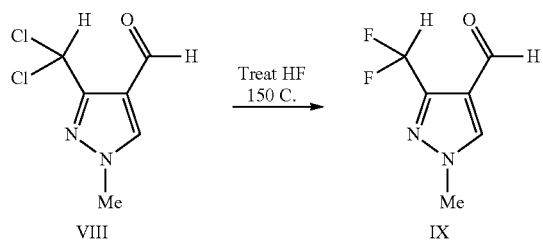

3-Dichloromethyl-1-methyl-1H-pyrazole-4-carbaldehyde (1.94 g, compound of formula VIII) was charged to a Monel 100 ml pressure reactor followed by 20.1 g tris(hydrogen fluoride)-triethylamide by syringe. The system was sealed up and agitated whilst heating the contents to 150° C. After achieving the target temperature the reaction mass was held on temperature for 2 h. The reaction mass was then allowed to stand overnight and cool before it was quenched. Quenching was effected by drowning out the reactor contents (black liquid) into water (50 ml). The quenched reaction mass was then extracted with methyl-t-butyl ether (2×25 ml). After separating the organic phases were washed with brine and the organic layer was dried with magnesium sulphate, filtered and concentrated under vacuo to give the compound of formula IX in the form of a red/brown oil (0.38 g); yield ~40%. The product was analysed by GC and GCMS.

GCMS: 42, 51, 69, 77, 83, 112, 131, 141, 159, 160 (M$^+$)

The invention claimed is:

1. A process for the preparation of a compound of formula (I)

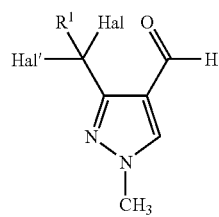

(I)

wherein Hal and Hal' are independently selected from Cl and F, and R$^1$ is selected from Cl, F and H, comprising reacting a compound of formula (II) with a Vilsmeier reagent

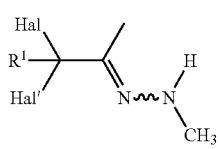

(II)

wherein Hal, Hal' and R$^1$ are as defined above.

2. The process according to claim 1 wherein Hal and Hal' are F.

3. The process according to claim 1 wherein Hal and Hal' are Cl.

4. The process according to claim 1 wherein R$^1$ is H.

5. The process according to claim 1 wherein R$^1$ is F.

6. The process according to claim 1 comprising the further step of oxidizing the compound of formula (I) to give a carboxylic acid of formula (VI)

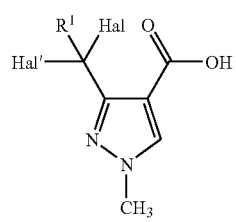

(VI)

wherein Hal, Hal' and R$^1$ are as defined in claim 1 or a salt form thereof.

7. The process according to claim 6 wherein the oxidant is hydrogen peroxide.

8. The process according to claim 6 wherein the oxidation is conducted in the presence of base.

9. The process according to claim 3, comprising a step of halogen exchange to convert Hal and Hal' from Cl to F.

10. The process according to claim 1 wherein the Vilsmeier reagent is generated in situ from POCl$_3$ and dimethylformamide.

11. The process according to claim 1 wherein the compound of formula (II) is generated by the reaction of a ketone of formula (VII)

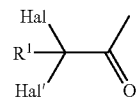

(VII)

wherein Hal, Hal' and R$^1$ are as defined in claim 1 with methyl hydrazine.

* * * * *